(12) United States Patent
Ishida et al.

(10) Patent No.: US 10,504,621 B2
(45) Date of Patent: Dec. 10, 2019

(54) MEDICAL IMAGE PROCESSING APPARATUS, MEDICAL IMAGING APPARATUS AND IMAGE ARCHIVING APPARATUS

(71) Applicant: Toshiba Medical Systems Corporation, Otawara-shi (JP)

(72) Inventors: Katsuhiko Ishida, Nasushiobara (JP); Tatsuya Watanabe, Nasushiobara (JP); Kazuki Gatayama, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 169 days.

(21) Appl. No.: 15/854,429

(22) Filed: Dec. 26, 2017

(65) Prior Publication Data

US 2018/0182480 A1    Jun. 28, 2018

(30) Foreign Application Priority Data

Dec. 28, 2016 (JP) .................. 2016-255027
Dec. 22, 2017 (JP) .................. 2017-246007

(51) Int. Cl.
  *G16H 30/20* (2018.01)
  *G06T 7/11* (2017.01)
  *G06T 11/00* (2006.01)
  *G16H 30/40* (2018.01)

(52) U.S. Cl.
  CPC .............. *G16H 30/20* (2018.01); *G06T 7/11* (2017.01); *G06T 11/003* (2013.01); *G06T 11/008* (2013.01); *G16H 30/40* (2018.01); *G06T 2207/10081* (2013.01); *G06T 2207/10088* (2013.01); *G06T 2210/41* (2013.01)

(58) Field of Classification Search
  None
  See application file for complete search history.

(56) References Cited

U.S. PATENT DOCUMENTS

| 5,384,643 | A  | * | 1/1995  | Inga ...................... G06F 19/321 |
|           |    |   |         | 358/1.9                                 |
| 6,633,674 | B1 | * | 10/2003 | Barnes .................. G06T 3/4084   |
|           |    |   |         | 375/E7.013                              |
| 7,050,639 | B1 | * | 5/2006  | Barnes ................... H04N 19/13   |
|           |    |   |         | 375/E7.144                              |
| 7,224,839 | B2 | * | 5/2007  | Zeineh .................... G06T 9/007  |
|           |    |   |         | 348/14.13                               |
| 7,596,258 | B2 | * | 9/2009  | Fujisawa .................. G06T 7/66   |
|           |    |   |         | 345/1.1                                 |
| 8,837,860 | B1 | * | 9/2014  | Grady ...................... G06T 5/50  |
|           |    |   |         | 382/284                                 |

(Continued)

FOREIGN PATENT DOCUMENTS

| JP | 2007-89871   | 4/2007  |
| JP | 2007-275125  | 10/2007 |
| JP | 2009-254690  | 11/2009 |

*Primary Examiner* — Fayyaz Alam

(74) *Attorney, Agent, or Firm* — Oblon, McClelland, Maier & Neustadt, L.L.P.

(57) ABSTRACT

According to one embodiment, a medical image processing apparatus includes processing circuitry. The processing circuitry is configured to extract a first medical image relating to a region of interest from a second medical image. The processing circuitry is configured to add, to the second medical image, reconstruction matrix information added to the first medical image.

8 Claims, 11 Drawing Sheets

(56) References Cited

U.S. PATENT DOCUMENTS

| | | | |
|---|---|---|---|
| 2002/0057850 A1* | 5/2002 | Sirohey | G06T 3/4084 |
| | | | 382/299 |
| 2010/0054564 A1* | 3/2010 | Vija | G06T 5/002 |
| | | | 382/131 |
| 2015/0199121 A1* | 7/2015 | Gulaka | G16H 40/63 |
| | | | 715/771 |
| 2017/0061620 A1* | 3/2017 | Park | G06T 5/001 |
| 2018/0165867 A1* | 6/2018 | Kuhn | B33Y 50/00 |

* cited by examiner

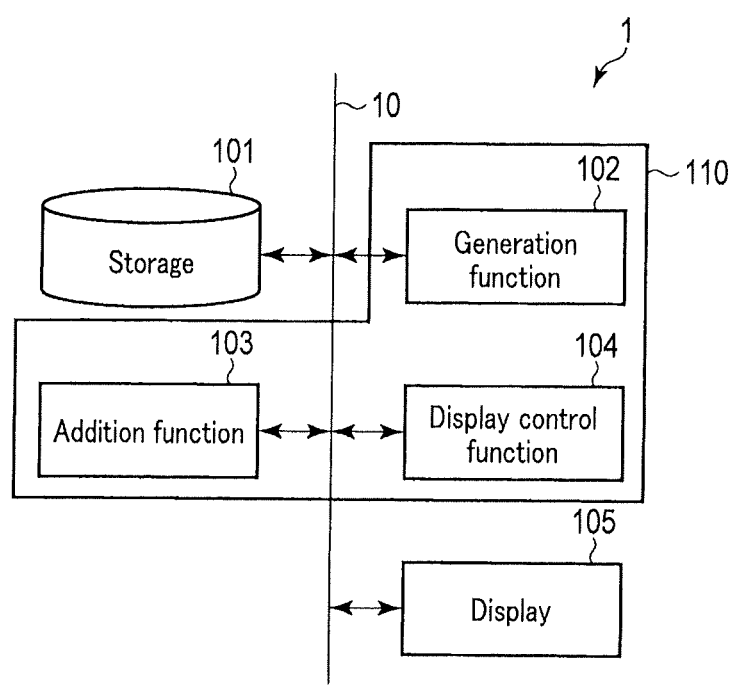
F I G. 1

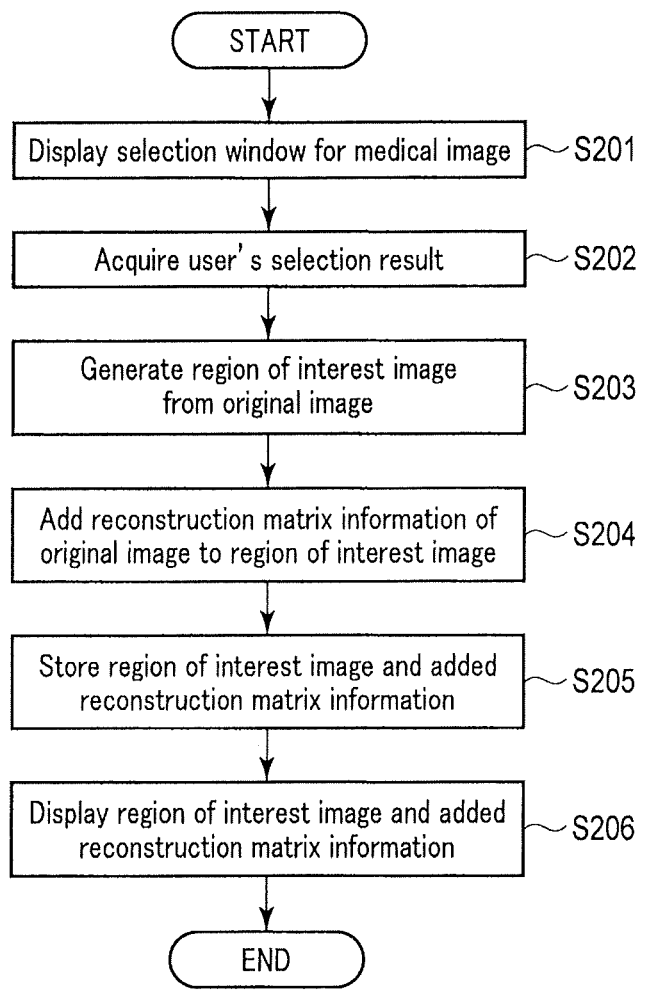
F I G. 2

Study

| Study | Examination date | ID | Name | Gender | Age | Examination part | P | Acv |
|---|---|---|---|---|---|---|---|---|

301

Series

| Series | IMG | Contrast | Type | Appl.Type | SureIQ_1 | SureIQ_2 | Comments | Matrix | P | Acv |
|---|---|---|---|---|---|---|---|---|---|---|

302

Image

| No | Mode | Scanned time | Start position/End position | Slice width | Gating information | Matrix | Reconstruction matrix | P | Acv |
|---|---|---|---|---|---|---|---|---|---|
| A |  |  |  |  |  | 1024 | 1024 |  |  |
| B |  |  |  |  |  | 2048 | 2048 |  |  |
| C |  |  |  |  |  | 512 | 512 |  |  |
| ... |  |  |  |  |  |  |  |  |  |

303 — 304, 305

F I G. 3

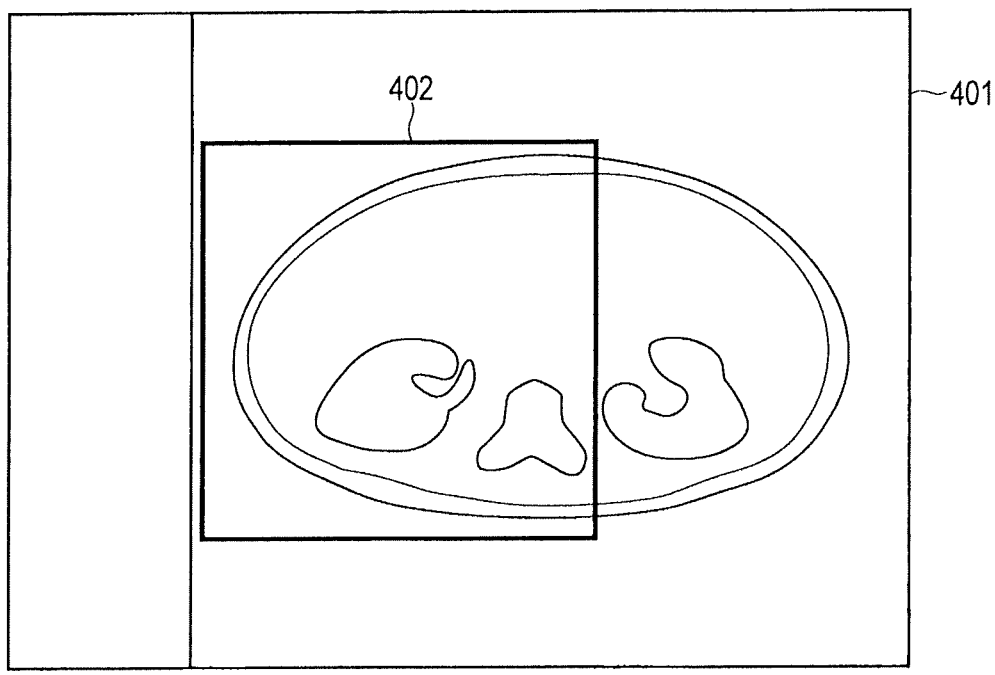
F I G. 4
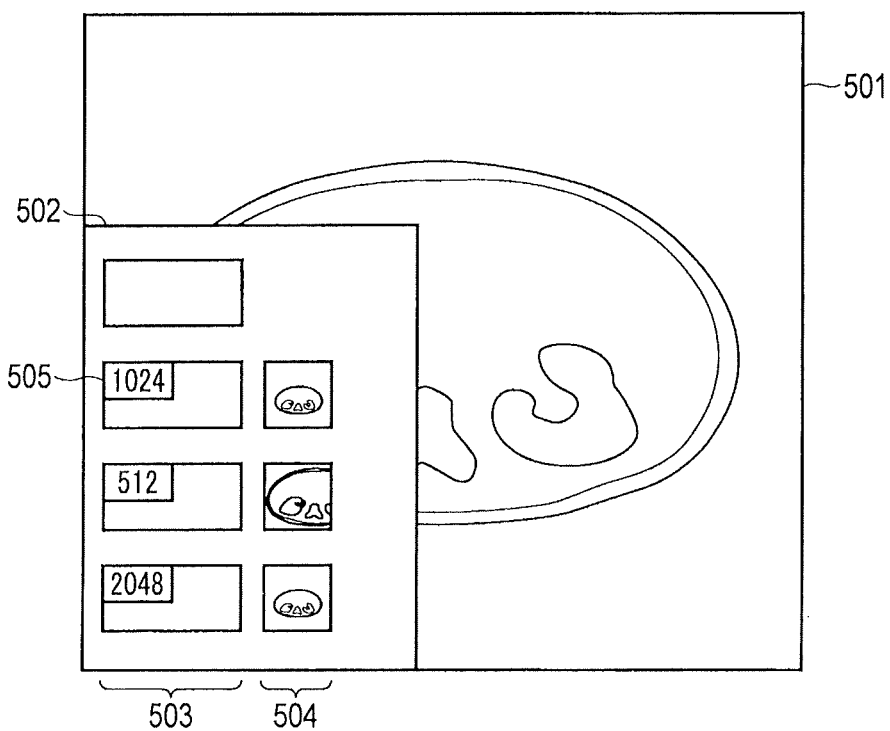
F I G. 5

MEDICAL IMAGE PROCESSING APPARATUS, MEDICAL IMAGING APPARATUS AND IMAGE ARCHIVING APPARATUS

CROSS-REFERENCE TO RELATED APPLICATIONS

This application is based upon and claims the benefit of priority from the prior Japanese Patent Application No. 2016-255027, filed Dec. 28, 2016, and No. 2017-246007, filed Dec. 22, 2017, the entire contents of all of which are incorporated herein by reference.

FIELD

Embodiments described herein relate generally to a medical image processing apparatus, a medical imaging apparatus and an image archiving apparatus.

BACKGROUND

For medical tomographic images such as CT images or MRI images, tomographic images having an image matrix size of 512×512 pixels are utilized as standard images. In conjunction with recent medical image resolution enhancement, tomographic images of high resolution having an image matrix size of 1024×1024 pixels or 2048×2048 pixels have been obtainable.

Since such resolution enhancement was not assumed conventionally, there is a possibility that tomographic images of 1024×1024 pixels cannot be applied due to the capacity of a Picture Archiving and Communication System (PACS), etc., and merely images having image matrix information of 512×512 pixels can be archived. A method for compressing an image of high resolution to an image of 512×512 pixels may be adopted, but the method may sacrifice the resolution. Accordingly, it is necessary to extract and store a partial region of an image having image matrix information of 512×512 pixels from an image having image matrix information of 1024×1024 pixels or 2048×2048 pixels. In this case, an original image of the extracted image may not be specified.

BRIEF DESCRIPTION OF THE DRAWINGS

FIG. 1 is a block diagram showing the configuration of a medical image processing apparatus according to the first embodiment.

FIG. 2 is a flowchart showing the operation of the medical image processing apparatus according to the first embodiment.

FIG. 3 shows an example of a selection window.

FIG. 4 shows the details of extraction processing.

FIG. 5 shows an example of an image display interface window.

DETAILED DESCRIPTION

Figure 6:
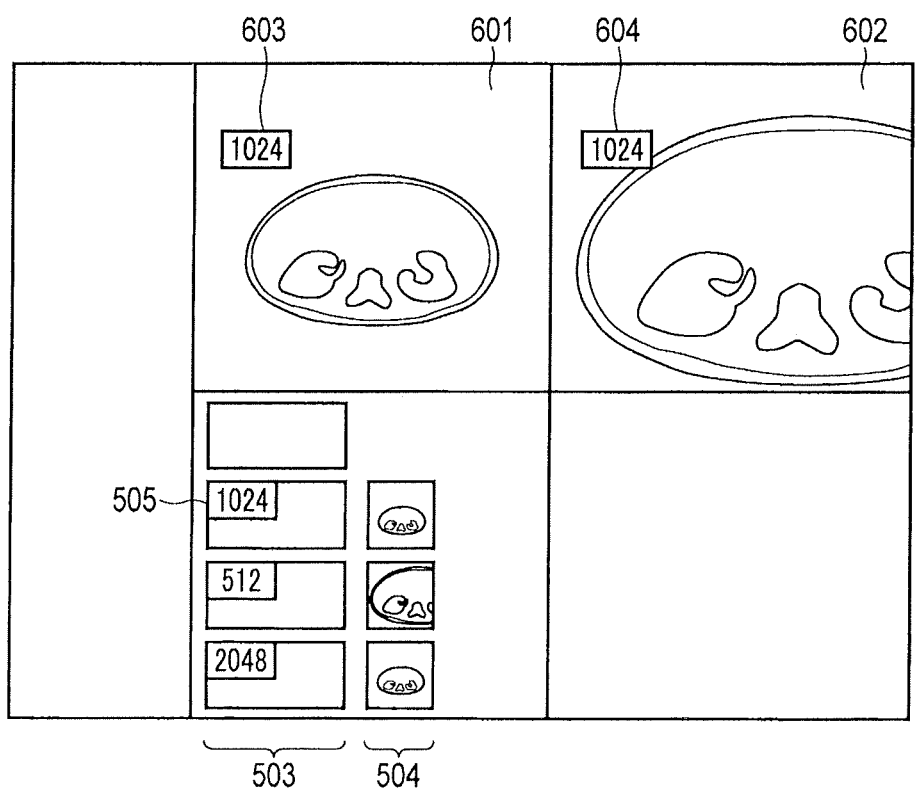
FIG. 6 shows an example where an original image and a region of interest image are displayed in parallel.

In general, according to one embodiment, a medical image processing apparatus includes processing circuitry. The processing circuitry is configured to extract a first medical image relating to a region of interest from a second medical image. The processing circuitry is configured to add, to the second medical image, reconstruction matrix information added to the first medical image.

In the following description, the medical image processing apparatus, a medical imaging apparatus and an image archiving apparatus according to the embodiments will be explained with reference to the drawings. In the embodiments described below, elements assigned with the same reference symbols perform the same operations, and redundant descriptions thereof will be omitted as appropriate.

First Embodiment

A medical image processing apparatus according to the first embodiment will be described with reference to the block diagram shown in FIG. 1.

The medical image processing apparatus 1 includes a storage 101, processing circuitry 110, and a display 105. A signal is transmitted and received via a bus 10.

The storage 101 which is, for example, a memory stores image data. It is assumed here that the image data is data of DICOM (digital imaging and communication in medicine) format, which includes a medical image, metadata added to the medical image, and a region of interest image (first medical image) described below. The metadata includes image matrix information and reconstruction matrix information. The image matrix information indicates the image matrix size of a medical image. The reconstruction matrix information indicates image matrix information of an image (original image or second medical image) from which the region of interest image is extracted. If the region of interest image is generated by multiple times of step-by-step extraction, the reconstruction matrix information indicates image matrix information of an original medical image. For the original image, the image matrix information and the reconstruction matrix information are identical.

The processing circuitry 110 is, for example, a processor, which executes a generation function 102, an addition function 103, and a display control function 104.

The processing circuitry 110, by executing the generation function 102, refers to image data stored in the storage 101, extracts a region of interest from the original image, and generates a region of interest image.

The processing circuitry 110, by executing the addition function 103, adds metadata of the original image to the region of interest image generated by executing the generation function 102. The metadata includes at least reconstruction matrix information.

The processing circuitry 110, by executing the display control function 104 allows the display 105 to display an interface window, and controls display of the medical image, the metadata, and the region of interest image. The display control function 104 controls a display mode of the medical image, the metadata, and the region of interest image, in accordance with a user's instruction. The display control function 104 may display the medical image, the metadata, and the region of interest image on an external display device connected through a network, etc.

The display 105 displays the medical image, the metadata, and the region of interest image.

The operation example of the medical image processing apparatus 1 according to the first embodiment will be explained with reference to the flowchart of FIG. 2.

In step S201, the processing circuitry 110, by executing the display control function 104, displays a selection window through which a medical image is selected on the display 105. The selection window displays at least the medical image and the metadata.

In step S202, the user selects a medical image to which execution processing is to be performed, and the processing circuitry 110 acquires, by executing the generation function 102, a selection result.

In step S203, the processing circuitry 110 performs, by executing the generation function 102, extraction processing from the medical image selected by the user, which is an original image, to generate a region of interest image.

In step S204, the processing circuitry 110 adds, by executing the addition function 103, image matrix information of the region of interest image and reconstruction matrix information of the original image to the region of interest image. The image matrix information of the original image may be added to the region of interest image.

In step S205, the storage 101 stores the region of interest image and the added image matrix information and reconstruction matrix information.

In step S206, the processing circuitry 110 displays, by executing the display control function 104, the image matrix information of the region of interest image and the reconstruction matrix information added in step S203 together with the region of interest image.

An example of the selection window displayed on the display 105 will be described with reference to FIG. 3.

FIG. 3 is an interface screen relating to the selection window of a medical image. The interface screen includes display windows such as a study information display window 301, a series information display window 302, and an image information display window 303. The image information display window 303 displays image matrix information 304 and reconstruction matrix information 305 in addition to a scanned time, an identification number, and a start position/end position which each are associated with a medical image.

In the case where a region of interest image is generated, the region of interest image is stored in the storage 101 as series information different from the original image. Specifically, the series information of the region of interest image is stored as different series information just below the series information of the original image.

The extraction processing in step S203 will be described in detail with reference to FIG. 4.

FIG. 4 is an interface screen relating to the extraction processing. The user moves an extraction window 402 superimposed on a medical image 401 by a cursor or by dragging a mouse so that a region of interest is settled within the extraction window 402. By settling the extraction window 402, the region of interest image is extracted. Since the image matrix size of the region of interest image is assumed to be 512×512 pixels, the extraction window 402 is fixed to the size of 512×512 pixels. Specifically, if the original image is the size of 1024×1024 pixels, a quarter of the original image size corresponds to 512×512 pixels.

A display example of a medical image will be described with reference to FIGS. 5 and 6.

FIG. 5 is an example of an image display interface screen in which an image selection window 502 (image selector) is superimposed on a medical image 501. The image selection window 502 includes series information 503 (series comment) and a thumbnail 504 of a medical image for each series. The series information 503 includes image matrix information 505. In the example shown in FIG. 5, a numerical value of image matrix information is displayed as a label (badge display). The display format of a label (color, font-size, etc.) may be changed in accordance with the image matrix information.

In the case where the extraction processing is performed, the series information and the thumbnail of the region of interest image generated as series information different from that of the original image are displayed just below the series information and the thumbnail of the original image. In the example shown in FIG. 5, it is assumed that the extraction processing is performed on an original image which is a medical image having a thumbnail corresponding to the series information (1024×1024 pixels) shown in the top of the image selection window 502, and a region of interest image is generated. In this case, the series information (512×512 pixels) and a corresponding thumbnail are displayed just below the original image.

FIG. 6 shows an example where an original image and a region of interest image are displayed in parallel.

Reconstruction matrix information 603 added to an original image 601 is displayed within a display area of the original image 601. Similarly, reconstruction matrix information 604 added to a region of interest image 602 is displayed within a display area of the region of interest image 602.

The reconstruction matrix, which is the metadata, is displayed so as to easily determine whether a medical image having a different image matrix size is an original image, or a region of interest image extracted from the original image.

For example, in the example shown in FIG. 6, the image display screen shows that the image matrix information of the original image 601 indicates 1024×1024 pixels, and the image matrix information of the region of interest image 602 indicates 512×512 pixels. On the other hand, the reconstruction matrix information of the original image 601 and the region of interest image 602 both indicate 1024×1024 pixels. Accordingly, it can be easily understood that the region of interest image 602 is not originally obtained at the image matrix size of 512×512 pixels, but is extracted from a medical image originally obtained at the image matrix size of 1024×1024 pixels. In addition, the resolution of the extracted region of interest image can be predicted from the reconstruction matrix information.

Figure 7:
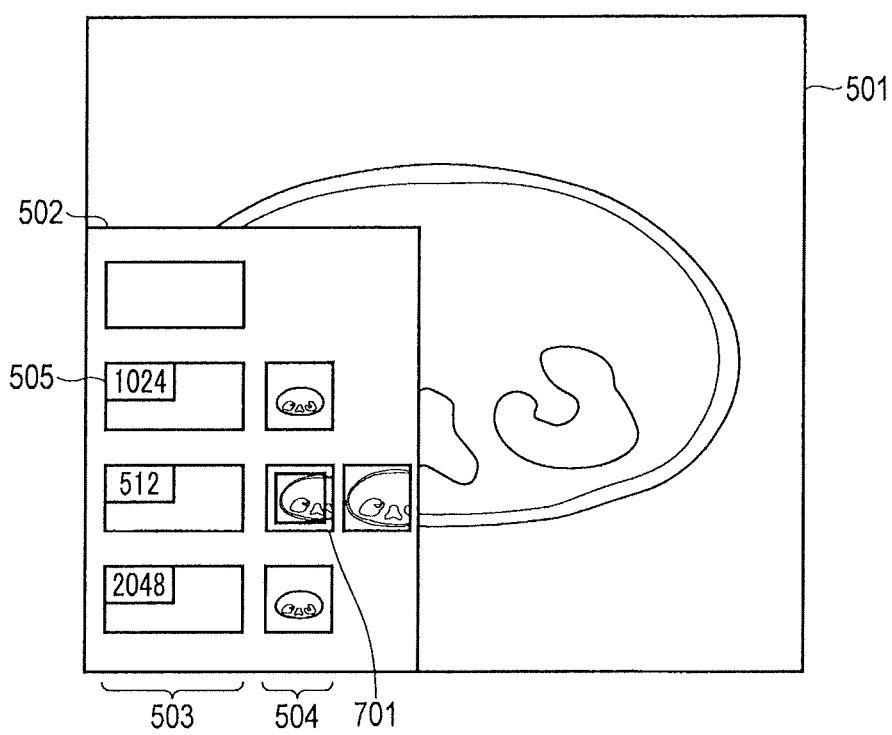
FIG. 7 shows an example of storing an image of an extracted region.

An image that indicates which region of the original image is extracted as the region of interest image may be stored separately. FIG. 7 shows an example of storing an image of an extracted region.

As shown in FIG. 7, by executing the generation function 102, the processing circuitry 110 may acquire an extraction position image 701 on which the extraction window 402 is superimposed as shown in FIG. 4 as a thumbnail, and may display the extraction position image 701 at a head of thumbnails regarding the region of interest image, for example. By this processing, the relationship between the original image and the region of interest image can be easily realized.

With the structure where the image matrix information 505 is displayed, the user can easily realize the image matrix size of a medical image of each series.

In the case where the extraction processing is performed multiple times, there may be a case where an image of 1024×1024 pixels is extracted from an image of 2048×2048 pixels, and an image of 512×512 pixels is extracted from the extracted 1024×1024 pixels image. In such a case, an image from which the extraction processing is firstly performed is set to be an original image, and reconstruction matrix information of the original image is added to the region of interest image. That is, the reconstruction matrix information of the original medical image is inherited to the region of interest image.

According to the first embodiment, at least reconstruction matrix information of the metadata of the original image is added to the region of interest image extracted from the original image so that the user can easily realize that the region of interest image is extracted from a given image. That is, for example, even in the case where the extraction processing is performed since the original image cannot be stored in the PACS, etc. due to the image size indicated by its image matrix information, the user can realize the original image from which the extracted image is obtained. In other words, it is possible to easily identify that the region of interest image is extracted from an image with high resolution, and accordingly to process the image easily depending on the purpose such as diagnostic reading or archiving.

Second Embodiment

The second embodiment of the present embodiment will be described with reference to FIG. 8.

Figure 8:
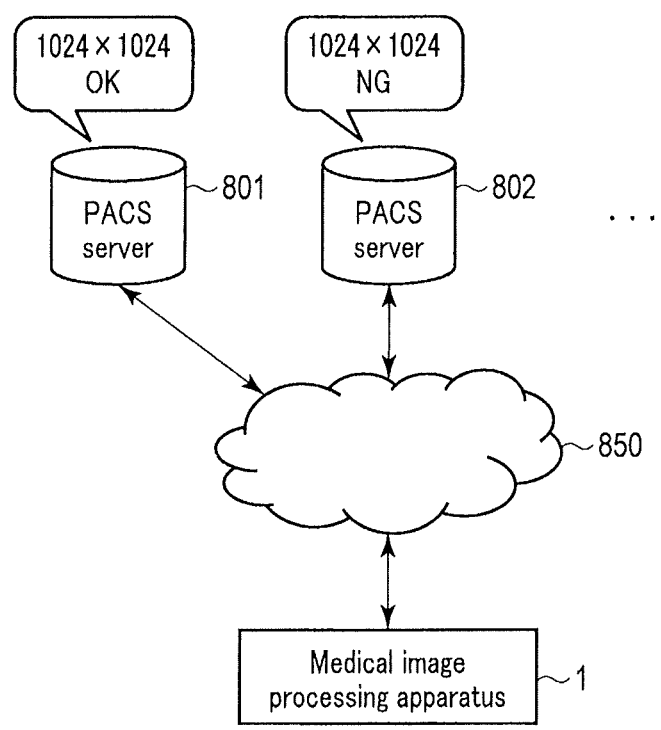
FIG. 8 is a conceptual drawing of the second embodiment.

As shown in FIG. 8, a plurality of servers that store an image, for example, a plurality of PACS servers 801 and 802, and a medical image processing apparatus 1 are connected to each other to be communicatable through a network 850.

In the case where it is not assumed that image matrix information of tomographic images is different, it may be the case where the PACS servers are different in the image matrix size that the respective PACS servers are capable of storing. For example, it may be assumed that the PACS server 801 is capable of storing a medical image of high resolution of 1024×1024 pixels; on the other hand, the PACS server 802 is not capable of storing an image of the resolution higher than 512×512 pixels, such as an image of 1024×1024 pixels.

In the second embodiment, a PACS server pre-stores image matrix information indicating the size of an image that the PACS server can store, and if the PACS server attempts to store a medical image having the image matrix information that the PACS server cannot store, notification and extraction processing are performed.

A medical image processing apparatus according to the second embodiment will be described with reference to the block diagram shown in FIG. 9.

The medical image processing apparatus 1 according to the second embodiment includes a correspondence table 901, a notification function 902, and an output function 903 in addition to the configuration of the medical image processing apparatus 1 according to the first embodiment.

The correspondence table 901 is a table indicating the image matrix information of an image that a PACS server of a transfer destination can store.

When an instruction for storing a medical image in a PACS server is performed by a user, the processing circuitry 110 refers, by executing the notification function 902, to the correspondence table 901 to determine whether the PACS server can store the medical image, and notifies a message to suggest extraction processing to the user if the PACS server cannot store the medical image.

The processing circuitry 110 outputs, by executing the output function 903, a region of interest image obtained by the extraction processing and metadata to the PACS server.

An example of the correspondence table 901 will be described with reference to FIG. 10.

Figures 9, 10:
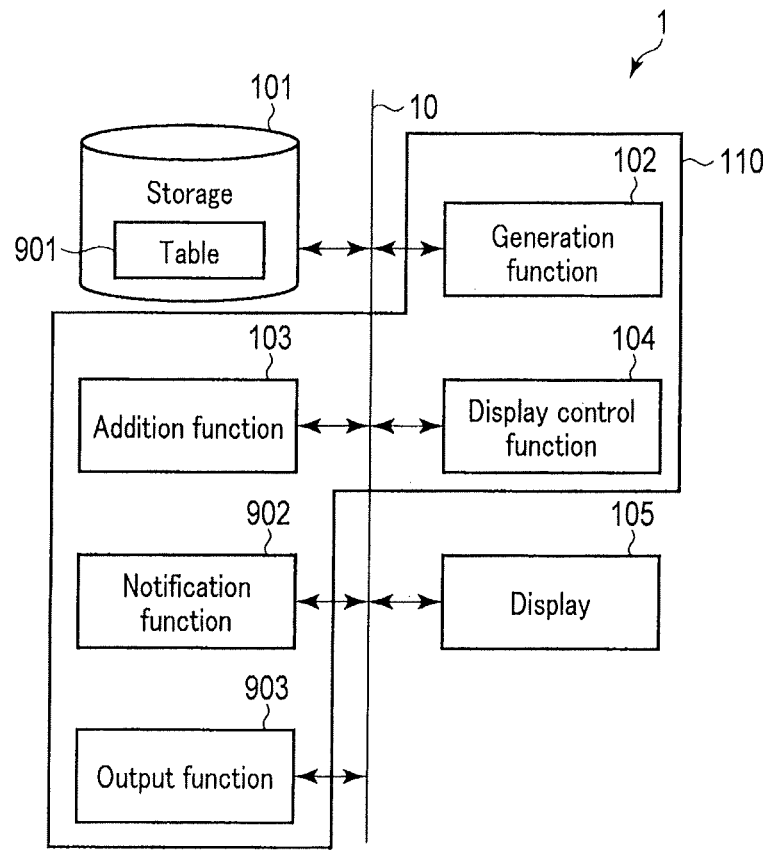
FIG. 9 is a block diagram showing the configuration of a medical image processing apparatus according to the second embodiment.
FIG. 10 shows an example of a correspondence table.

A correspondence table 1000 shown in FIG. 10 associates a server ID with an image matrix size that the corresponding server can store. For example, according to the correspondence table 1000, the PACS server of a server ID, "1", can store an image of all the matrix sizes; on the other hand, the PACS server of a server ID, "3", can store an image of the matrix sizes of 512×512 pixels and 1024×1024 pixels, but cannot store an image of the matrix size of 2048×2048 pixels.

Figure 11:
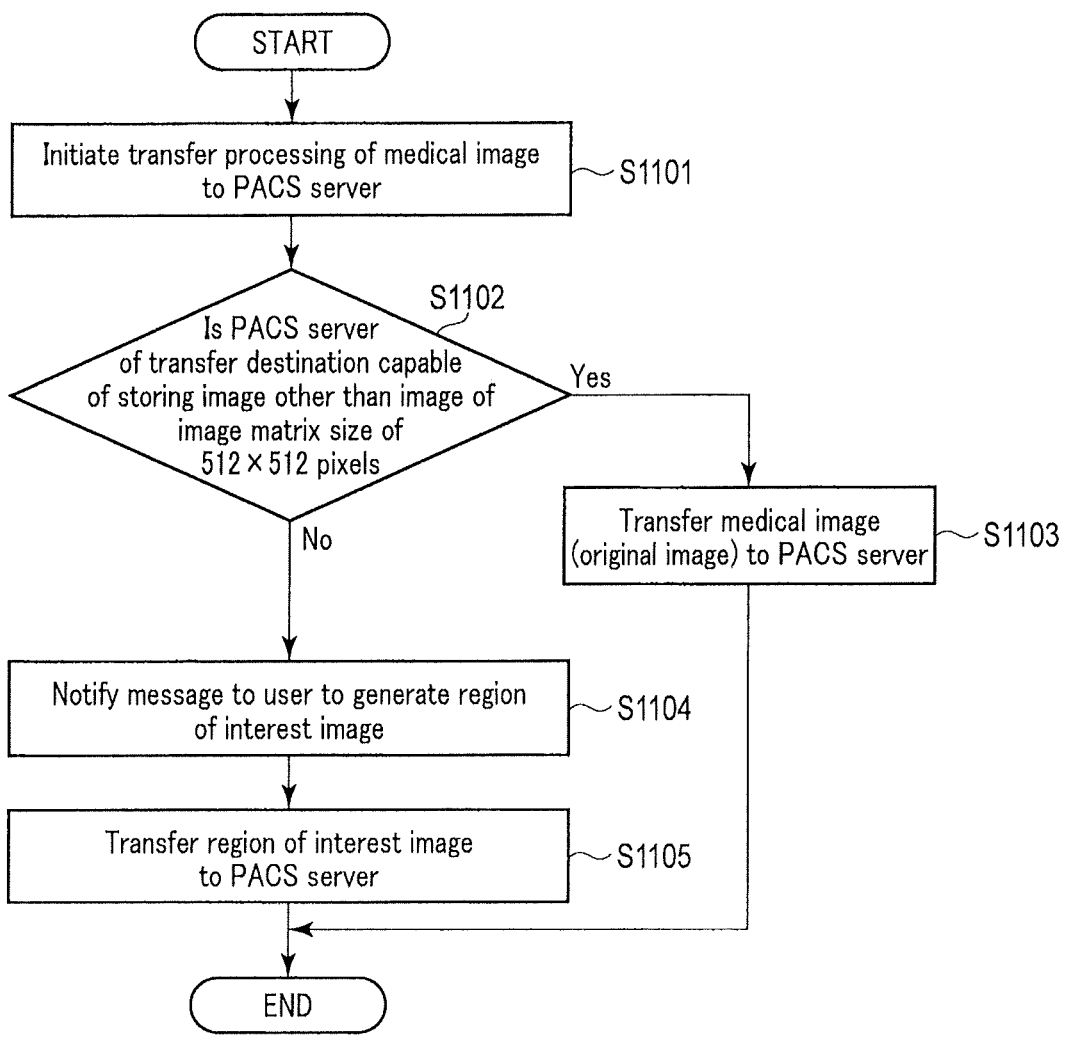
FIG. 11 is a flowchart showing the operation of the medical image processing apparatus according to the second embodiment.

The operation of the medical image processing apparatus 1 according to the second embodiment will be explained with reference to the flowchart of FIG. 11.

In step S1101, transfer processing of a medical image to a PACS server is initiated upon receipt of a user's instruction to store the medical image to the PACS server, or upon completion of image pick-up processing.

In step S1102, the processing circuitry 110 determines, by executing the notification function 902, whether or not the PACS server that is a transfer destination is capable of storing an image other than an image of image matrix information of 512×512 pixels. The determination can be made by referring to the table. If it is determined that the destination PACS server is capable of storing the image, the processing proceeds to step S1103. If not, the processing proceeds to step S1104.

In step S1103, the medical image (original image) and the metadata are transferred to the PACS server.

In step S1104, the processing circuitry 110 notifies, by executing the notification function 902, a message to a user in order to suggest performing execution processing to generate a region of interest image. It may be preset that the generation function extracts a predetermined region and generates a region of interest image.

In step S1105, the processing circuitry 110 transfers, by executing the output function 903, the region of interest image and the metadata including the reconstruction matrix information of the original image to the PACS server. The operation of the medical image processing apparatus 1 according to the second embodiment is terminated by the above processing.

If the image matrix size that the PACS server is capable of storing can be changed in real time at the PACS server, the processing described below can be performed. For example, transfer restriction information that indicates the image matrix size that the PACS server is capable of storing is transmitted to the medical image processing apparatus 1 at predetermined intervals, or at the timing when an instruction for storing an image is made by a user. The processing circuitry 110 may determine, by executing the notification function 902, whether or not extraction processing is performed based on the transfer restriction information.

The original image and the metadata may be deleted upon completion of transferring the region of interest image to the PACS server, or after the storage 101 stores the original image and the metadata for a predetermined period.

According to the second embodiment, the extraction processing is performed by referring to the correspondence table that indicates the image matrix size of an image that the destination server is capable of storing, thereby generating a medical image (region of interest image) according to the capable matrix size, and suitably storing the medical image in the server. That is, it is possible to easily process the image depending on the purpose, such as diagnostic reading or archiving.

Third Embodiment

The medical image processing apparatus according to the first or second embodiment may be implemented in an X-ray computed tomography (CT) apparatus, for example, as a medical image pick-up apparatus.

In the third embodiment, the medical image processing apparatus is included in an X-ray CT apparatus. However, the third embodiment can be applied to the case where the medical image processing apparatus is included in another multi-modality, such as an MR. In addition, the medical image processing apparatus can be adopted for a work station or PACS, etc., that does not include a reconstruction processing function.

X-ray CT apparatus that includes a medical image processing apparatus according to the third embodiment will be explained with reference to FIG. 12.

Figure 12:
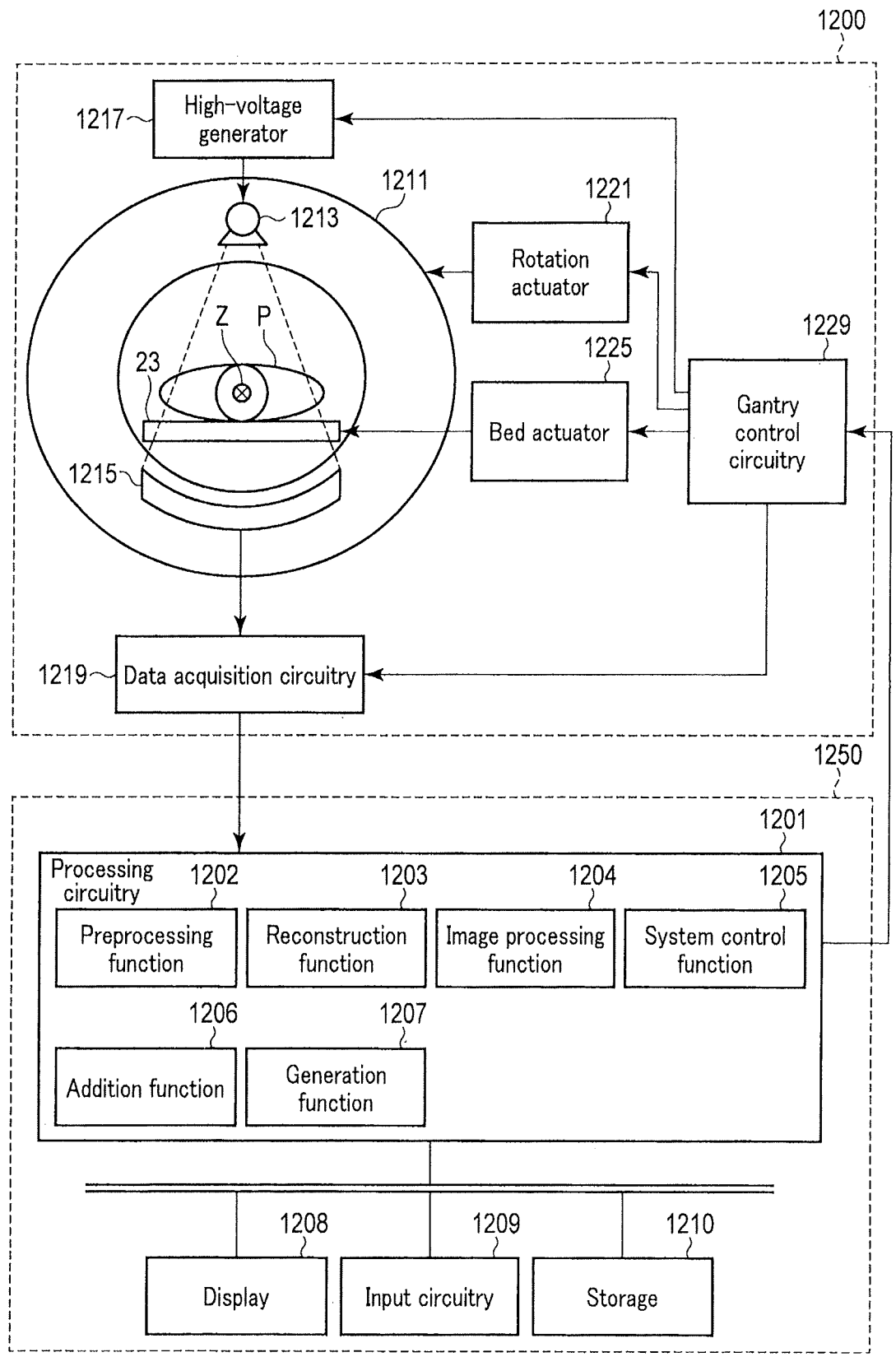
FIG. 12 is a diagram showing the configuration of an X-ray CT apparatus that includes a medical image processing apparatus according to the third embodiment.

FIG. 12 shows a configuration of the X-ray computed tomography apparatus according to the present embodiment. As shown in FIG. 12, the X ray computed tomography apparatus of the present embodiment includes a gantry 1200 and a console 1250. For example, the gantry 1200 is placed in a CT examination room, and the console 1250 is placed in a control room adjacent to the CT examination room. The gantry 1200 and the console 1250 are connected communicatably to each other. The gantry 1200 includes an image pick-up mechanism configured to perform X-ray CT imaging of a subject P. The console 1250 is a computer that controls the gantry 1200.

As shown in FIG. 12, the gantry 1200 includes a rotation frame 1211 of an essentially cylindrical shape, which includes a bore. The rotation frame 1211 is also referred to as a rotation unit. As shown in FIG. 1, an X-ray tube 1213 and an X-ray detector 1215 which are arranged to face each other via the bore are attached to the rotation frame 1211. The rotation frame 1211 is a metal frame made of, for example, aluminum, in an annular shape. As will be explained below in detail, the gantry 1200 includes a main frame made of metal, such as aluminum. The main frame is also referred to as a stationary unit. The rotation frame 1211 is rotatably supported by the main frame.

The X-ray tube 1213 generates an X-ray. The X-ray tube 1213 includes a vacuum tube with a cathode that generates thermoelectrons and an anode that generates X-rays by receiving the thermoelectrons traveled from the cathode. The X-ray tube 1213 is connected to a high-voltage generator 1217 via a high-voltage cable. The high-voltage generator 1217 is attached, for example, to the rotation frame 1211. The high-voltage generator 1217 generates a high voltage to be applied to the X-ray tube 1213 and supplies a filament heating current, in accordance with the control of gantry control circuitry 1229. The high voltage is applied between an anode and a cathode housed in the X-ray tube 1213. The filament heating current is applied to the cathode of the X-ray tube 1213. The high voltage applied between the anode and the cathode of the X-ray tube 1213 is referred to as a tube voltage. A flow of thermoelectrons that is generated from the cathode heated by the filament heating current and traveled to the anode under the high voltage is referred to as a tube current. The high-voltage generator 1217 adjusts the tube voltage and the tube current to the X-ray tube 1213 in accordance with an X-ray condition.

The rotation frame 1211 rotates about the center axis Z at a predetermined angular velocity upon receiving power from a rotation actuator 1221. A direct drive motor, a servo motor, etc. is used as the rotation actuator 1221. The rotation actuator 1221 is housed, for example, in the gantry 1200. Upon receiving a driving signal from the gantry control circuitry 1229, the rotation actuator 1221 generates power to rotate the rotation frame 1211.

An field of view (FOV) is set in the bore of the rotation frame 1211. A top plate supported by a bed 1223 is inserted into the bore of the rotation frame 1211. The subject P is placed on the top plate. The bed 1223 movably supports the top plate. A bed actuator 1225 is housed in the bed 1223. Upon receiving a driving signal from the gantry control circuitry 1229, the bed actuator 1225 generates power to move the top plate in the longitudinal direction, the vertical direction, and the widthwise direction. The bed 1223 regulates the top plate so that an imaging target portion of the subject P is included within an FOV.

The X-ray detector 1215 detects X-rays generated by the X-ray tube 1213. Specifically, the X-ray detector 1215 includes a plurality of detection elements arranged on a two-dimensional curved surface. Each of the detection elements includes a scintillator and a photoelectric conversion element. The scintillator is formed of a material that converts X-rays into light. The scintillator converts the applied X-rays into photons of the number corresponding to the intensity of the applied X-rays. The photoelectric conversion element is a circuit element that amplifies light received from the scintillator and converts the received light into an electrical signal. For example, a photomultiplier tube or a photodiode is applied as the photoelectric conversion element. The detection element may be an indirect detection type detection element that converts X-rays into light and then detects the light, as described above, or a direct conversion type detection element that directly converts X-rays into an electrical signal.

The X-ray detector 1215 is connected to data acquisition circuitry 1219. In accordance with the instruction from the gantry control circuitry 1229, the data acquisition circuitry 1219 reads from the X-ray detector 1215 an electrical signal corresponding to the intensity of X-rays detected by the X-ray detector 1215, and acquires raw data having a digital value corresponding to the dose of X-rays during a view period. The data acquisition circuitry 1219 acquires electrical signals read according to the resolution of the reconstruction image as a bundle. The data acquisition circuitry 1219 is implemented by, for example, an Application Specific Integrated Circuit (ASIC) on which a circuit element that is capable of generating raw data is mounted.

The gantry control circuitry 1229 synchronously controls the high-voltage generator 1217, the data acquisition circuitry 1219, the rotation actuator 1221, and the bed actuator 1225, to perform X-ray CT imaging in accordance with imaging conditions obtained from the processing circuitry 1201 of the console 1250. The gantry control circuitry 1229 includes a processor, such as a Central Processing Unit (CPU) and a Micro Processing Unit (MPU), and a memory, such as a Read Only Memory (ROM) and a Random Access Memory (RAM), as hardware resources. The gantry control circuitry 1229 may be implemented as an ASIC or a Field Programmable Gate Array (FPGA), a Complex Programmable Logic Device (CPLD), or a Simple Programmable Logic Device (SPLD).

The console 1250 includes the processing circuitry 1201, a display 1208, an input circuitry 1209, and a storage 1210. Data communication is performed between the processing circuitry 1201, the display 1208, the input circuitry 1209, and the storage 1210 via a bus.

The processing circuitry 1201 includes a processor, such as a CPU, an MPU, or a Graphics Processing Unit (GPU), and a memory, such as a ROM or a RAM, etc. as hardware resources. The processing circuitry 1201 executes various programs to implement a preprocessing function 1202, a reconstruction function 1203, an image processing function 1204, a system control function 1205, an addition function 1206, and a generation function 1207.

By executing the preprocessing function 1202, the processing circuitry 1201 performs preprocessing such as logarithmic conversion to raw data transmitted from the gantry 1200. The preprocessed raw data is also referred to as projection data.

By executing the reconstruction function 1203, the processing circuitry 1201 generates a CT image representing a space distribution of CT values relating to the subject P based on the preprocessed raw data. The known image reconstruction algorithm such as a Filtered Back Projection (FBP) method or a successive approximation reconstruction method, may be adopted.

By executing the image processing function 1204, the processing circuitry 1201 performs various image processing to the CT image reconstructed by the reconstruction function 1203. For example, the processing circuitry 1201 performs three-dimensional image processing, such as volume rendering, surface volume rendering, image value projection processing, Multi-Planer Reconstruction (MPR) processing, Curved MPR (CPR) processing, etc. to the CT image to generate a display image.

By executing the system control function 1205, the processing circuitry 1201 comprehensively controls the medical image processing apparatus according to the present embodiment. Specifically, the processing circuitry 1201 reads a control program stored in the storage 1210, expands the control program in a memory, and controls the respective units of the X-ray computed tomography apparatus in accordance with the expanded control program. By executing the system control function 1205, the processing circuitry 1201 performs operations similar to those performed by the display control function 104 in the aforementioned embodiments.

The display 1208 and the storage 1210 each perform operations similar to those performed by the display 105 and the storage 101 in the aforementioned embodiments.

By executing the addition function 1206 and the generation function 1207, the processing circuitry 1201 performs operations similar to those performed by the addition function 103 and the generation function 102 in the aforementioned embodiments.

The preprocessing function 1202, the reconstruction function 1203, the image processing function 1204, the system control function 1205, the addition function 1206, and the generation function 1207 may be implemented by the processing circuitry 1201 on a single substrate, or may be implemented by the processing circuitry 1201 on a plurality of substrates.

According to the third embodiment, it is possible in the X-ray CT apparatus to easily identify that the region of interest image is extracted from an image with high resolution, and accordingly to easily process the image depending on the purpose such as diagnostic reading or archiving.

Fourth Embodiment

In the fourth embodiment, an image archiving apparatus includes the configuration of the medical image processing apparatus as stated above, and the image archiving apparatus performs extraction processing of an image.

The image archiving apparatus is a server archiving (storing) images. Hereinafter, as a concrete example, it is assumed that the image archiving apparatus is a PACS server.

Figure 13:
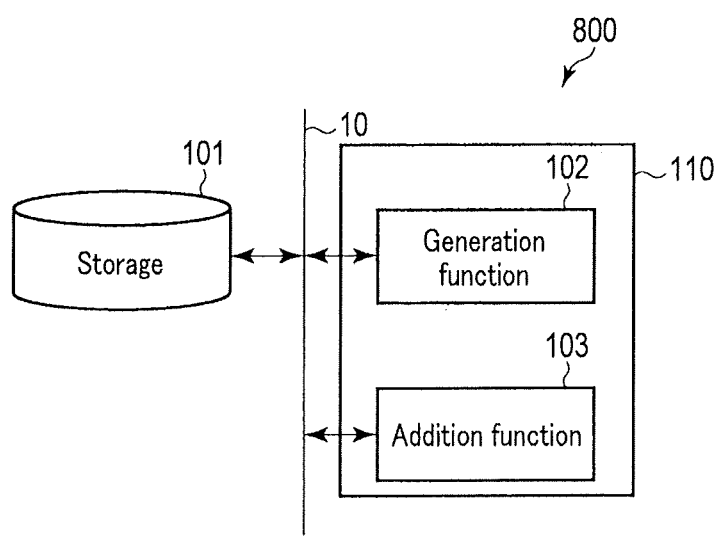
FIG. 13 is a block diagram showing the image archiving apparatus according to the fourth embodiment.

The PACS server according to the fourth embodiment will be described with reference to the block diagram shown in FIG. 13.

A PACS server 800 according to the fourth embodiment includes a storage 101 and processing circuitry 110. The processing circuitry 110 executes a generation function 102 and an addition function 103.

The operations of each circuitry and function in the PACS server 800 are similar to those explained in the above embodiments.

According to the fourth embodiment, the PACS server can perform extraction processing of an image when transferring the image to another server, which realizes flexible processing. That is, it is possible to easily process the image depending on the purpose.

The medical image processing apparatus explained in the above embodiments may be included in an image inspection device. The image inspection device performs inspection processing such as rearranging captured medical images in an order suitable to diagnostic reading. The image inspection device may implement the medical image processing apparatus as a part of the inspection processing. In addition, the image inspection device may include the function of the medical image processing apparatus and may implement the function.

Furthermore, the functions described in connection with the above embodiments may be implemented, for example, by installing a program for executing the processing in a computer, such as a work station, etc., and expanding the program in a memory. The program that causes the computer to execute the processing can be stored and distributed by means of a storage medium, such as a magnetic disk (a hard disk, etc.), an optical disk (CD-ROM, DVD, etc.), and a semiconductor memory.

While certain embodiments have been described, these embodiments have been presented by way of example only, and are not intended to limit the scope of the inventions. Indeed, the embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

What is claimed is:
1. A medical image processing apparatus comprising processing circuitry configured to:
   extract a first medical image relating to a region of interest from a second medical image; and
   add, to the first medical image, reconstruction matrix information added to the second medical image.

2. The apparatus according to claim 1, wherein the processing circuitry is further configured to display the reconstruction matrix information together with the first medical image.

3. The apparatus according to claim 2, wherein the processing circuitry further displays image matrix information of the first medical image.

4. The apparatus according to claim 1, further comprising:
a storage configured to store the first medical image, metadata added to the first medical image, the second medical image, and metadata added to the second medical image,
wherein the metadata includes the image matrix information and the reconstruction matrix information.

5. The apparatus according to claim 1, further comprising
a table that indicates an image matrix size of an image that each of a plurality of external servers is capable of storing,
wherein the processing circuitry is further configured, if a transfer instruction of an image to a first sever among the plurality of external servers is received, to determine whether or not the first servers is capable of storing the image by referring to the table, and if the first server is not capable of storing the image, to notify a message that suggests execution of processing to generate the first medical image.

6. The apparatus according to claim 1, wherein the reconstruction matrix information indicates image matrix information of the second medical image.

7. A medical image processing apparatus comprising processing circuitry configured to:
image a second medical image;
extract a first medical image relating to a region of interest from the second medical image; and
add to the first medical image reconstruction matrix information added to the second medical image.

8. An image archiving apparatus comprising:
processing circuitry configured to:
extract a first medical image relating to a region of interest from a second medical image; and
add to the first medical image reconstruction matrix information added to the second medical image; and
a storage configured to store the first medical image in which the reconstruction matrix information is added.

* * * * *